US012678242B2

(12) United States Patent
Noonan et al.

(10) Patent No.: US 12,678,242 B2
(45) Date of Patent: Jul. 14, 2026

(54) IMAGE GUIDED ROBOTIC CONVERGENT ABLATION

(71) Applicant: KONINKLIJKE PHILIPS N.V., Eindhoven (NL)

(72) Inventors: David Paul Noonan, New York, NY (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1390 days.

(21) Appl. No.: 16/065,870

(22) PCT Filed: Dec. 19, 2016

(86) PCT No.: PCT/IB2016/057762
§ 371 (c)(1),
(2) Date: Jun. 25, 2018

(87) PCT Pub. No.: WO2017/115212
PCT Pub. Date: Jul. 6, 2017

(65) Prior Publication Data
US 2019/0000575 A1      Jan. 3, 2019

Related U.S. Application Data

(60) Provisional application No. 62/272,412, filed on Dec. 29, 2015.

(51) Int. Cl.
*A61B 34/30* (2016.01)
*A61B 18/02* (2006.01)
(Continued)

(52) U.S. Cl.
CPC .............. *A61B 34/32* (2016.02); *A61B 18/02* (2013.01); *A61B 34/10* (2016.02); *A61B 34/20* (2016.02);
(Continued)

(58) Field of Classification Search
CPC ............ A61B 18/02; A61B 2018/0212; A61B 2034/104; A61B 2034/107;
(Continued)

(56) References Cited

U.S. PATENT DOCUMENTS 8,221,402 B2    7/2012  Christian
8,273,081 B2    9/2012  Viswanathan
(Continued)

FOREIGN PATENT DOCUMENTS

AU        2011312077 A1 *  5/2013    ......... A61F 9/00817
EP           2666432 A1    11/2013
(Continued)

OTHER PUBLICATIONS

Kumar et al., "Hybrid approach to atrial fibrillation ablation using bipolar radiofrequency devices epicardially and cryoballoon endocardially", Interactive CardioVascular and Thoracic Surgery (Year: 2014).*
(Continued)

*Primary Examiner* — Christopher L Cook

(57) ABSTRACT

A robotic system employing a plurality of surgical robots (20) and a surgical procedure controller (22) for executing a surgical procedure on an anatomical structure (e.g., a heart) within an anatomical region (e.g., a thoracic region). In operation, controller (22) autonomously controls a navigation of each surgical robot (20) within the anatomical region relative to the anatomical structure by directing a navigation of each surgical robot (20) within the anatomical region relative to the anatomical structure based on a surgical plan for executing the surgical procedure on the anatomical structure (e.g., a convergent ablation plan consisting of an epicardial ablation plan for abating an exterior of a heart and an endocardial ablation plan for ablating an interior of the heart) and further by revising the surgical plan responsive to a partial or complete inability of one or more of the surgical
(Continued)

robots (20) to be navigated within the anatomical region relative to the anatomical structure based on the surgical plan.

20 Claims, 12 Drawing Sheets

(51) Int. Cl.

| | |
|---|---|
| *A61B 34/10* | (2016.01) |
| *A61B 34/20* | (2016.01) |
| *A61B 34/32* | (2016.01) |
| *B25J 9/16* | (2006.01) |
| *G16H 20/40* | (2018.01) |
| *A61B 90/00* | (2016.01) |

(52) U.S. Cl.

CPC ............. *A61B 34/30* (2016.02); *B25J 9/1666* (2013.01); *G16H 20/40* (2018.01); *A61B 2018/0212* (2013.01); *A61B 2034/104* (2016.02); *A61B 2034/107* (2016.02); *A61B 2034/2051* (2016.02); *A61B 2034/2055* (2016.02); *A61B 2034/2065* (2016.02); *A61B 2034/301* (2016.02); *A61B 2090/062* (2016.02); *A61B 2090/08021* (2016.02); *A61B 90/361* (2016.02); *A61B 2090/376* (2016.02)

(58) Field of Classification Search

CPC .... A61B 2034/2051; A61B 2034/2055; A61B 2034/2065; A61B 2034/301; A61B 2090/062; A61B 2090/08021; A61B 2090/376; A61B 34/10; A61B 34/20; A61B 34/30; A61B 34/32; A61B 90/361; B25J 9/1666

See application file for complete search history.

(56) References Cited

U.S. PATENT DOCUMENTS

| | | | |
|---|---|---|---|
| 8,617,152 | B2 | 12/2013 | Flaherty |
| 8,641,710 | B2 | 2/2014 | Bunch |
| 8,696,658 | B2 | 4/2014 | Benetti |
| 8,965,496 | B2 | 2/2015 | Bailin |
| 9,033,885 | B2 | 5/2015 | Arenson |
| 9,821,455 | B1 * | 11/2017 | Bareddy .................. H04N 7/15 |
| 9,833,254 | B1 * | 12/2017 | Barral .................... A61B 90/30 |
| 10,398,501 | B2 * | 9/2019 | Willard ............. A61B 18/1492 |
| 10,716,958 | B2 * | 7/2020 | Neff ....................... A61B 34/30 |
| 2005/0273200 | A1 * | 12/2005 | Hietmann .......... G05B 19/4061 |
| | | | 700/248 |
| 2007/0185485 | A1 | 8/2007 | Hauck |
| 2007/0198008 | A1 | 8/2007 | Hauck |
| 2009/0149867 | A1 | 6/2009 | Glozman |
| 2010/0114094 | A1 | 5/2010 | Arenson |
| 2010/0185087 | A1 | 7/2010 | Nields |
| 2012/0004547 | A1 | 1/2012 | Barley |
| 2012/0165652 | A1 | 6/2012 | Dempsey |
| 2012/0226145 | A1 | 9/2012 | Chang |
| 2013/0282005 | A1 | 10/2013 | Brost |
| 2013/0317363 | A1 | 11/2013 | Case |
| 2014/0022250 | A1 | 1/2014 | Comaniciu |
| 2014/0058407 | A1 * | 2/2014 | Tsekos ................... A61B 34/30 |
| | | | 606/130 |
| 2014/0201669 | A1 * | 7/2014 | Liu ........................ A61B 34/10 |
| | | | 715/771 |
| 2014/0330108 | A1 | 11/2014 | Dempsey |
| 2015/0119671 | A1 | 4/2015 | Varma |
| 2015/0366624 | A1 * | 12/2015 | Kostrzewski .......... A61B 90/11 |
| | | | 606/130 |
| 2016/0066768 | A1 | 3/2016 | Popovic |
| 2016/0220307 | A1 * | 8/2016 | Miller ............... A61B 18/1233 |

FOREIGN PATENT DOCUMENTS

| | | | |
|---|---|---|---|
| WO | 2007141784 | A2 | 12/2007 |
| WO | WO 2012/047991 | * | 4/2012 |
| WO | 2012088321 | A1 | 6/2012 |

OTHER PUBLICATIONS

Khan et al., "A framework for a fault tolerant multi-robot systsem" IEEE, Jul. 2015 (Year: 2015).*

Hu et al., "Semi-autonomous Simulated Brain Tumor Ablation with RavenII Surgical Robot using Behavior Tree", 2015 IEEE International Conference on Robotics and Automation (ICRA), Seattle, Washington, May 26-30, 2015 (Year: 2015).*

Kiser et al., "Advantages of the Convergent Procedure", Mar. 2014 (Year: 2014).*

* cited by examiner $$M_{T_R} = {}^IT_R * M_{T_I}$$

128

165

Convergent
ablation tracker
160c

184b

186a

186b

186c

186d

186e

186f

186g

Convergent
ablation verifier
160d

IMAGE GUIDED ROBOTIC CONVERGENT ABLATION

CROSS-REFERENCE TO PRIOR APPLICATIONS

This application is the U.S. National Phase application under 35 U.S.C. § 371 of International Application No. PCT/IB2016/057762, filed on Dec. 19, 2016, which claims the benefit of U.S. Provisional Patent Application No. 62/272,412, filed on Dec. 29, 2015. These applications are hereby incorporated by reference herein.

FIELD OF THE INVENTION

The present disclosure generally relates to a hybrid procedure for performing an endo-surgical procedure on an interior of an anatomical structure and an epi-surgical procedure on an exterior of the anatomical structure, particularly a convergent ablation for performing a combined endocardial ablation and epicardial ablation for treating any type of cardiac arrhythmia (e.g., atrial fibrillation). The present disclosure specifically relates to a robotic control of an execution of a hybrid procedure under image guidance based on an endo-surgical procedure plan and an epi-surgical procedure plan.

BACKGROUND OF THE INVENTION

Endocardial catheter ablation in patients with longstanding persistent atrial fibrillation (AF) is associated with limited levels of success, especially in the presence of structural heart disease. This is due to the complexity of isolating all the necessary electrical pathways using an ablation catheter inside the heart.

Epicardial surgical approaches (e.g., Cox Maze procedure), have been shown to be successful in treating AF. However, the invasive nature of such approaches has limited the use of epicardial surgical approaches. In addition, minimally invasive epicardial approaches (e.g., "mini-maze" procedure) have not resulted in the success rates of open chest procedures.

An emerging technique is the "hybrid procedure", which has been developed to perform combined endocardial catheter ablation and epicardial ablation under direct surgeon vision to create a comprehensive lesion pattern both inside and outside the heart. More particularly, during a hybrid procedure, a multidisciplinary team plans the ablation pattern taking into account the relative 'strengths and weaknesses' of the two different ablation approaches.

Executing complex convergent ablation plans has proved to be challenging, particularly in an assurance that the regions ablated by the different strategies are complementary and achieve the goal of electrical isolation of the affected regions. The challenges exist for both manual ablation (i.e. manual catheter manipulation and manual surgical tool manipulation) and for robotic-assisted ablation.

SUMMARY OF THE INVENTION

The present disclosure provides inventive systems, controllers and methods for autonomously controlling a navigation of a plurality of surgical robots within an anatomical region relative to an anatomical structure to thereby execute a planned surgical procedure on the anatomical structure. For example, an autonomous control of a navigation of an epicardial ablation robot and an endocardial ablation robot within a thoracic region relative to a heart to thereby execute a planned convergent ablation of the heart.

One form of the inventions of the present disclosure is a robotic system employing a plurality of surgical robots and a surgical procedure controller for executing a surgical procedure on an anatomical structure (e.g., a heart) within an anatomical region (e.g., a thoracic region). In operation, the surgical procedure controller autonomously controls a navigation of each surgical robot within the anatomical region relative to the anatomical structure by directing a navigation of each surgical robot within the anatomical region relative to the anatomical structure based on a surgical plan for executing the surgical procedure on the anatomical structure (e.g., a convergent ablation plan consisting of an epicardial ablation plan for abating an exterior of a heart and an endocardial ablation plan for ablating an interior of the heart) and further by revising the surgical plan responsive to a partial or complete inability of one or more of the surgical robots to be navigated within the anatomical region relative to the anatomical structure based on the surgical plan.

A second form of the inventions of the present disclosure is a robotic system employing an epi-surgical robot (e.g., a epicardial ablation robot), an endo-surgical robot (e.g., an endocardial ablation robot) and a hybrid procedure controller (e.g., a convergent ablation controller).

In operation, the hybrid procedure controller directs a navigation of the epi-surgical robot within the anatomical region relative to the anatomical structure based on an epi-surgical procedure plan for executing the surgical procedure adjacent an exterior of the anatomical structure, and directs a navigation of the endo-surgical robot within the anatomical region relative to the anatomical structure based on an endo-surgical procedure plan for executing the surgical procedure within an interior of the anatomical structure.

Further in operation, the hybrid procedure controller revises the epi-surgical procedure plan responsive to a partial or a complete inability of the endo-surgical robot to be navigated within the anatomical region relative to the anatomical structure based on the endo-surgical procedure plan, and/or revises the endo-surgical procedure plan responsive to a partial or a complete inability of the epi-surgical robot to be navigated within the anatomical region relative to the anatomical structure based on the epi-surgical procedure plan.

Particularly for a convergent ablation of a heart, a convergent ablation controller directs a navigation of an epicardial ablation robot within a thoracic region relative to a heart based on an epicardial ablation plan for operating the epicardial ablation robot to ablate an exterior of the heart, and directs a navigation of the endocardial ablation robot within the thoracic region relative to the heart based on the endocardial ablation plan for operating the endocardial ablation robot to ablate an interior of the heart.

Further in operation, the convergent ablation controller revises the epicardial ablation plan responsive to a partial or a complete inability of the endocardial ablation robot to be navigated within the thoracic region relative to the heart based on the endocardial ablation plan, and/or revises the endocardial ablation plan responsive to a partial or a complete inability of the epicardial ablation robot to be navigated within the thoracic region relative to the heart based on the epicardial ablation plan.

A third form of the inventions of the present disclosure is a modular network of the surgical procedure controller including a planner, a navigator and a tracker.

In operation, the planner generates and revises (if applicable) a surgical plan for executing the surgical procedure on the anatomical structure;

The navigator directs a navigation of each surgical robot within the anatomical region relative to the anatomical structure based on the surgical plan; and The tracker directs a revision of the surgical plan by the planner responsive to a partial or a complete inability one or more of the surgical robots to be navigated within the anatomical region relative to the anatomical structure based on the surgical plan.

A fourth form of the inventions of the present disclosure is a modular network of the hybrid procedure controller including a planner, a navigator, and a tracker.

In operation, the planner generates the epi-surgical procedure plan for executing the surgical procedure adjacent an exterior of the anatomical structure, and generates the endo-surgical procedure plan for executing the surgical procedure within an interior of the anatomical structure.

The navigator directs the navigation of the epi-surgical robot within the anatomical region relative to the anatomical structure based on the epi-surgical procedure plan, and directs the navigation of the endo-surgical robot within the anatomical region relative to the anatomical structure based on the endo-surgical procedure plan.

The tracker directs a revision by the planner of the epi-surgical procedure plan responsive to a partial or a complete inability of the endo-surgical robot to be navigated within the anatomical region relative to the anatomical structure based on the endo-surgical procedure plan, and/or directs a revision by the planner of the endo-surgical procedure plan responsive to a partial or a complete inability of the epi-surgical robot to be navigated within the anatomical region relative to the anatomical structure based on the epi-surgical procedure plan.

Particularly for a convergent ablation of a heart, the planner generates an epicardial ablation plan for operating the epicardial robot to ablate an exterior of the heart, and generates an endocardial ablation plan for operating the endocardial robot to ablate an interior of the heart.

The navigator directs a navigation of the epicardial ablation robot within the thoracic region relative to the heart based on the epicardial ablation plan, and directs a navigation of the endocardial ablation robot within the thoracic region relative to the heart based on the endocardial ablation plan.

The tracker directs a revision by the planner of the epicardial ablation plan responsive to a partial or a complete inability of the endocardial ablation robot to be navigated within the thoracic region relative to the heart based on the endocardial ablation plan, and/or directs a revision by the planner of the endocardial ablation plan responsive to a partial or a complete inability of the epicardial ablation robot to be navigated within the thoracic region relative to the heart based on the epicardial ablation plan.

A fifth form of the inventions of the present disclosure is a method for operating a surgical procedure controller to autonomously control a navigation of a plurality of surgical robots within an anatomical region relative to an anatomical structure.

The method involves the surgical procedure controller directing a navigation of each surgical robot within the anatomical region relative to the anatomical structure based on a surgical plan for executing the surgical procedure on the anatomical structure, and The method further involves the surgical procedure controller revising the surgical plan responsive to a partial or a complete inability of one or more of the surgical robots to be navigated within the anatomical region relative to the anatomical structure based on the surgical plan.

A sixth form of the inventions of the present disclosure is a method of operating a surgical procedure controller to autonomously control a navigation of an epi-surgical robot and an endo-surgical robot within an anatomical region (e.g., a heart) relative to an anatomical structure (e.g., a thoracic region).

The method involves the surgical procedure controller generating an epi-surgical plan for executing the surgical procedure adjacent an exterior of the anatomical structure (e.g., an ablation of the exterior of a heart by the epi-surgical robot) and generating an endo-surgical plan for executing the surgical procedure within an interior of the anatomical structure (e.g., an ablation of an interior of a heart by the endo-surgical robot).

The method further involves the surgical procedure controller directing a navigation of the epi-surgical robot within the anatomical region relative to the anatomical structure based on the epi-surgical plan, and directing a navigation of the endo-surgical robot within the anatomical region relative to the anatomical structure based on the endo-surgical plan.

The method further involves the surgical procedure controller revising the epi-surgical plan responsive to at least a partial inability of the endo-surgical robot to be navigated within the anatomical region relative to the anatomical structure based on the endo-surgical plan, and revising the endo-surgical plan responsive to at least a partial inability of the epi-surgical robot to be navigated within the anatomical region relative to the anatomical structure based on the epi-surgical plan.

For purposes of the present disclosure, (1) the terms "anatomical structure" and "anatomical region" are terms of the art of the present disclosure as exemplary described herein. Examples of an anatomical structure include, but are not limited to, organs and bone. Examples of an anatomical region include, but are not limited to a cranial region, a nasal region, a thoracic region, an abdominal region, a dorsal region, a lumbar region and a cervical region;

(2) the terms "surgical procedure", "hybrid procedure" and "convergent ablation procedure" are terms of the art of the present disclosure;

(3) the term "surgical robot" broadly encompasses any robot having a structural configuration, as understood in the art of the present disclosure and as exemplary described herein, equipped with a surgical tool/instrument (e.g., a saw, a laser, scissors, an ablation catheter etc.) for performing any type of surgical procedure within an anatomical region;

(4) the term "epi-surgical robot" broadly encompasses any robot having a structural configuration, as understood in the art of the present disclosure and as exemplary described herein, for performing any type of surgical procedure adjacent an exterior of an anatomical structure, and the term "epicardial ablation robot" broadly encompasses any robot having a structural configuration, as understood in the art of the present disclosure and as exemplary described herein, for performing an epicardial ablation procedure;

(5) the term "endo-surgical robot" broadly encompasses any robot having a structural configuration, as understood in the art of the present disclosure and as exemplary described herein, for performing any type of surgical procedure within an interior of an anatomical structure, and the term "endocardial ablation robot" broadly encompasses any robot having a structural configuration, as understood in the art of the present disclosure and as exemplary described herein, for performing an endocardial ablation procedure;

(6) the term "controller" broadly encompasses all structural configurations as understood in the art of the present disclosure and as exemplary described herein of an application specific main board or an application specific integrated circuit for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s) and port(s). The controller may be housed or linked to a workstation. Examples of a workstation include, but are not limited to, an assembly of one or more computing devices (e.g., a client computer, a desktop and a tablet), a display/monitor, and one or more input devices (e.g., a keyboard, joysticks and mouse). Any descriptive labeling of the a controller herein (e.g., a "surgical procedure" controller, a "hybrid procedure" controller, a "convergent ablation" controller, etc.) serves to identify a particular controller as described and claimed herein without specifying or implying any additional limitation to the term "controller";

(7) the term "module" broadly encompasses a component of the controller consisting of an electronic circuit and/or an executable program (e.g., executable software and/firmware) for executing a specific application. Any descriptive labeling of an application module herein (e.g., a "a planner" module, a "navigator" module, a "tracker" module, a "verifier" module etc.) serves to identify a particular application module as described and claimed herein without specifying or implying any additional limitation to the term "application module";

(8) the term "anatomical mapping system" broadly encompasses any system as understood in the art of the present disclosure and as exemplary described herein, for generating any type of mapping an anatomical structure, and the term "electric mapping system" broadly encompasses any system, as understood in the art of the present disclosure and as exemplary described herein, for generating an electric map of an anatomical structure based on an electrophysiology technique. An example of an electric mapping system include, but are not limited to, the Carto® 3 System, (9) the term "medical imaging system" broadly encompasses any system, as understood in the art of the present disclosure and as exemplary described herein, utilized for imaging purpose during any type of medical/surgical procedure, and the term "ablation imaging system" broadly encompasses any system, as understood in the art of the present disclosure and as exemplary described herein, suitable for imaging purpose during an ablation procedure. Examples of an imaging system include, but are not limited to, an X-ray imaging system, a computed tomography imaging system, a magnetic resonance imaging system, an ultrasound imaging system, and an endoscopic imaging system,

(10) additional terms of the art, including but are not limited to, "ablation catheter", "articulated robot", "navigation", "image", "report" and "plan" and any tenses thereof broadly encompass such terms as understood in the art of the present disclosure and as exemplary described herein,

(11) any descriptive labeling of an additional term of the art serves to identify that particular term of the art as described and claimed herein without specifying or implying any additional limitation to that term of the art", and

(12) the term "revising" or any tense thereof broadly encompasses, as understood in the art of the present disclosure and as exemplary described herein, a modification, an adaptation and a substitution.

The foregoing forms and other forms of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION OF THE PREFERRED EMBODIMENTS

Figure 1:
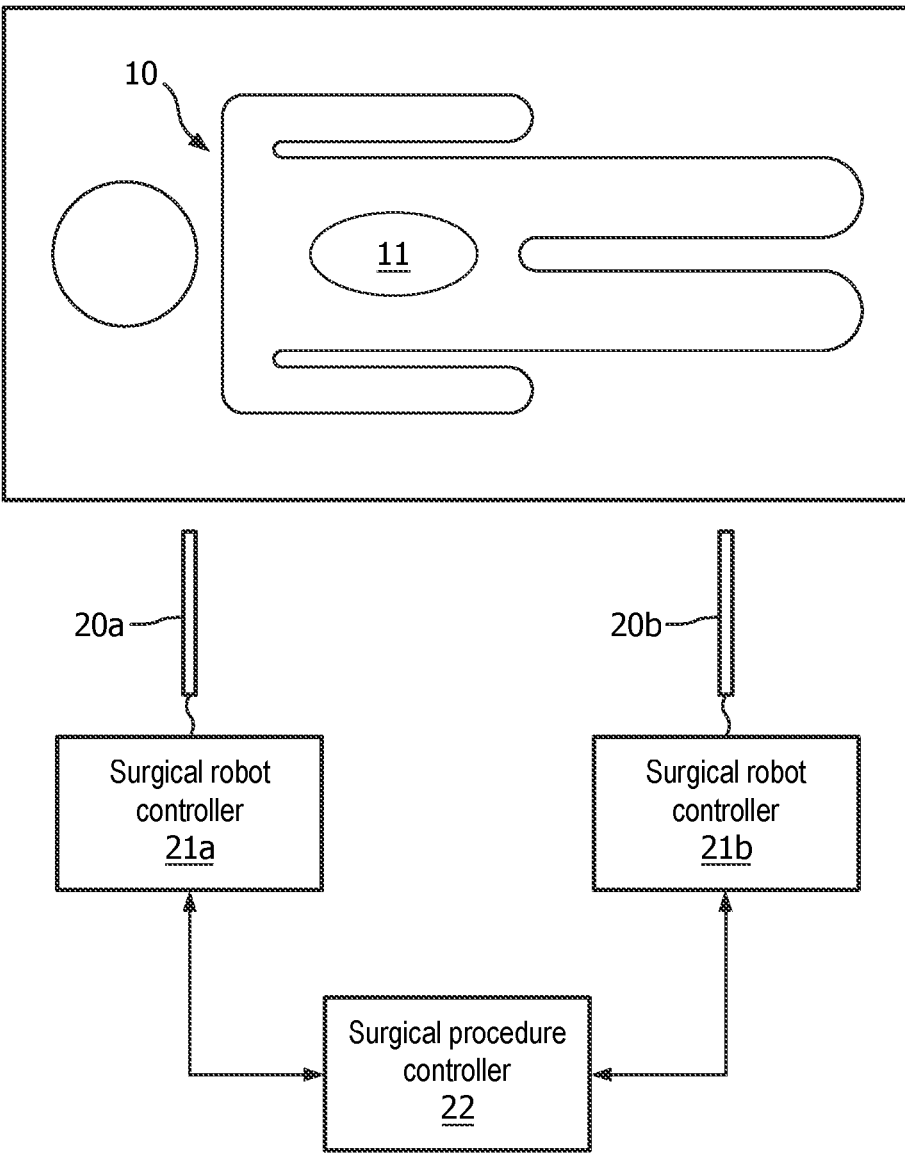
FIG. 1 illustrates an exemplary embodiment of a surgical procedure system in accordance with the inventive principles of the present disclosure.

To facilitate an understanding of the present disclosure, the following description of FIG. 1 teaches basic inventive principles of an image guidance based autonomous robotic control of a surgical procedure on any anatomical structure (e.g., an organ or a bone structure symbolized as anatomical structure 11) within any anatomical region of patient 10 (e.g., a cranial region, a nasal region, a thoracic region, an abdominal region, a dorsal region, a lumbar region and a cervical region) of a patient 10. From this description, those having ordinary skill in the art will appreciate how to apply the inventive principles of the present disclosure to various surgical procedures incorporating image guidance based autonomous robotic control of two (2) or more complementary surgical robots.

Referring to FIG. 1, a hybrid procedure incorporates two or more surgical robots 20 (of which surgical robots 20*a* and 20*b* are shown), a surgical robot controller 21 for each surgical robot 20 (of which surgical robot controller 21*a* and 21*b* are shown) and a hybrid procedure controller 22 for autonomous control of the hybrid procedure. The hybrid procedure involves a single port incision or multiple port incisions into an anatomical region of patient 10 whereby each surgical robot controller 21 may control a navigation of a corresponding surgical robot 20 within the anatomical region of patient 10 relative to a subject anatomical structure in accordance with a surgical plan generated by hybrid procedure controller 60 for executing the hybrid procedure on the subject anatomical structure, as will be further described herein for various embodiments of the present disclosure.

Each surgical plan delineates one or more surgical application of a corresponding surgical robot 20 within the anatomical region on the subject anatomical structure. For example, a surgical plan may specify a traversal of a surgical robot 20 across an interior or an exterior of the subject anatomical structure involving a surgical application (e.g., ablation, incision, etc.), as will be further described herein for various embodiments of the present disclosure.

During execution of the hybrid procedure, hybrid procedure controller 60 monitors the controlled navigation of each surgical robot 20 whereby hybrid procedure controller 60 revises the surgical plan as needed if one (1) or more of surgical robots 20 is(are), partially or fully, incapable of being navigated for whatever reason within the anatomical structure relative to the subject anatomical structure, as will be further described herein for various embodiments of the present disclosure.

Figure 2:
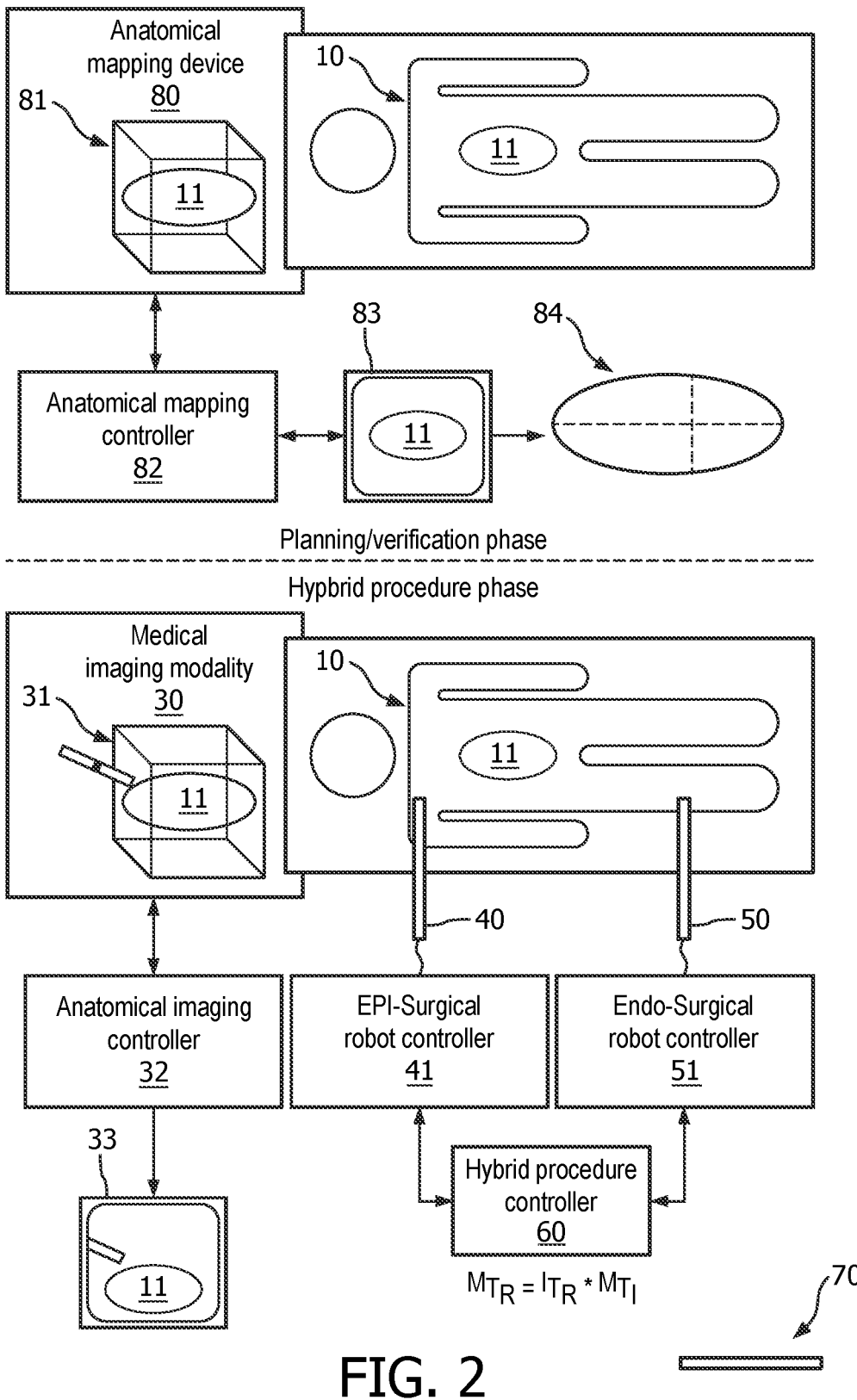
FIG. 2 illustrates an exemplary embodiment of hybrid procedure system in accordance with the inventive principles of the present disclosure.

To facilitate a further understanding of the present disclosure, the following description of FIG. 2 teaches basic inventive principles of an image guidance based autonomous robotic control of a hybrid procedure on any anatomical structure (e.g., an organ or a bone structure symbolized as anatomical structure 11) within any anatomical region of patient 10 (e.g., a cranial region, a nasal region, a thoracic region, an abdominal region, a dorsal region, a lumbar region and a cervical region) of a patient 10. From this description, those having ordinary skill in the art will appreciate how to apply the inventive principles of the present disclosure to various hybrid procedures incorporating image guidance based autonomous robotic control of a epi-surgical robot and endo-surgical robot.

Referring to FIG. 2, a planning/verification phase of the hybrid procedure incorporates an anatomical mapping system employing an anatomical mapping device 80, an anatomical mapping controller 82 and a monitor 83. Generally, anatomical mapping controller 82 controlling a generation by anatomical mapping device 80 of an anatomical map 81 of any anatomical structure 11 within any anatomical region of patient 10, and further controls a display as known in the art of anatomical map 81 of anatomical structure 11 on monitor 83 for zoning anatomical map 81 into a procedure zone map 84 for planning and verifying an epi-surgical procedure plan for traversing an epi-surgical robot 40 across an exterior of anatomical structure 11 and an endo-surgical procedure plan for traversing an endo-surgical robot 50 across an interior of anatomical structure 11

Still referring to FIG. 2, a hybrid phase of the hybrid procedure incorporates a medical imaging system employing an imaging modality 30 (e.g., an X-ray C-arm, a transesophageal echocardiography probe, a magnetic resonance imaging modality, computed tomography imaging modality, etc.), a procedure imaging controller 32 and a monitor 33. The hybrid procedure further incorporates epi-surgical robot 40, an epi-surgical robot controller 41, endo-surgical robot 50, an endo-surgical robot controller 51 and a hybrid procedure controller 60. Epi-surgical robot 40 and/or endo-surgical robot 50 50 may employ a catheter camera 70.

The hybrid procedure involves a single port incision or multiple port incisions into the anatomical region of patient 10 whereby epi-surgical robot controller 41 may autonomously control a navigation of epi-surgical robot 40 within the anatomical region of patient 10 in accordance with the epi-surgical procedure path generated by hybrid procedure controller 60 for traversing epi-surgical robot 40 across an exterior of anatomical structure 11. In practice, epi-surgical robot 40 may support a navigation of camera catheter 70 for live imaging of anatomical structure 11.

The hybrid procedure further involves a single port incision or multiple port incisions into patient 10 whereby endo-surgical robot controller 51 may autonomously control a navigation by of endo-surgical robot 50 within the anatomical region of patient 10 in accordance with a endo-surgical procedure path generated by hybrid procedure controller 60 for traversing endo-surgical robot 50 across an interior of anatomical structure 11. In practice, similarly, endo-surgical robot 50 may support a navigation of camera catheter 70 for live imaging of anatomical structure 11.

To execute a hybrid procedure of anatomical structure 11 as planned, epi-surgical robot 40 and endo-surgical robot 50 must be registered to anatomical map 81.

In one embodiment of the hybrid procedure, epi-surgical robot 40 (and optionally camera catheter 70) is manually or robotically inserted via epi-surgical robot controller 41 within the anatomical region of patient 10 adjacent anatomical structure 11 whereby medical imaging controller 32 controls a generation by medical imaging modality 31 of an anatomical image 31 illustrative epi-surgical robot 40 relative to anatomical structure 11 within the anatomical region of patient 10. If camera catheter 70 is deployed via epi-surgical robot 40, then a camera catheter controller (not shown) controls a display an endoscopic video view of anatomical structure 11 via camera catheter 70 on monitor 33 or an additional monitor as known in the art for positioning purposes of epi-surgical robot 40 relative to anatomical structure 11 of patient 10 and/or for registration purposes to anatomical map 81 and anatomical image 31.

The registration of articulated robot 40*c* to anatomical map 81 is accomplished by hybrid procedure controller 60 in accordance with the following equation [1a]:

$$^{M}T_{R}=^{I}T_{R}*^{M}T_{I} \tag{1a}$$

where $^{I}T_{R}$ is the transformation of epi-surgical robot 40 to anatomical image 31, where $^{M}T_{I}$ is the transformation of robotic image 21 to anatomical map 81, and where $^{M}T_{R}$ is the transformation of epi-surgical robot 40 to anatomical map 81.

Still referring to FIG. 2, upon the registration, epi-surgical robot controller 41 is capable of autonomously controlling a navigation of epi-surgical robot 40 within the anatomical region of patient 10 in accordance with a path traversing an exterior of anatomical structure 11 as planned by hybrid procedure controller 60. During the path traversal epi-surgical robot 40, medical imaging controller 32 controls a display of the navigation of epi-surgical robot 40 within the anatomical region as known in the art for visual feedback purposes.

In one embodiment of the hybrid procedure, endo-surgical robot 50 (and optionally camera catheter 70) is manually or robotically inserted via endo-surgical robot controller 51 within the anatomical region of patient 10 adjacent anatomical structure 11 whereby medical imaging controller 32 controls a generation by medical imaging modality 30 of an anatomical image 31 illustrative of endo-surgical robot 50 relative to anatomical structure 11 within the anatomical region of patient 10. If camera catheter 70 is deployed via articulated robot 50c, then a camera catheter controller (not shown) controls a display an endoscopic video view of anatomical structure 11 via camera catheter 70 on monitor 33 or an additional monitor as known in the art for positioning purposes of endo-surgical robot 50 relative to anatomical structure 11 of patient 10 and/or for registration purposes to anatomical map 81 and anatomical image 31.

The registration of articulated robot 50c to anatomical map 81 is accomplished by hybrid procedure controller 60 in accordance with the following equation [1b]:

$$^{M}T_{R} = {}^{I}T_{R} * {}^{M}T_{I} \qquad [1b]$$

where $^{I}T_{R}$ is the transformation of endo-surgical robot 50 to anatomical image 31, where $^{M}T_{I}$ is the transformation of robotic image 21 to anatomical map 81, and where $^{M}T_{R}$ is the transformation of endo-surgical robot 50 to anatomical map 81.

Still referring to FIG. 2, upon the registration, endo-surgical robot controller 51 is capable of autonomously controlling a navigation of endo-surgical robot 50 within the anatomical region of patient 10 in accordance with a path traversing an interior of anatomical structure 11 as planned by hybrid procedure controller 60. During the path traversal of endo-surgical robot 50, medical imaging controller 32 controls a display of the navigation of endo-surgical robot 50 within the anatomical region as known in the art for visual feedback purposes.

To facilitate an understanding of the present disclosure, the following description of FIGS. 3A-4D teaches basic inventive principles of an image guidance based autonomous robotic control of a convergent ablation procedure on a heart 12 within a thoracic region of patient 10. From this description, those having ordinary skill in the art will further appreciate how to apply the inventive principles of the present disclosure to various hybrid procedures incorporating image guidance based autonomous robotic control of complementary epicardial ablation robot and an endocardial ablation robot.

Figure 3A:
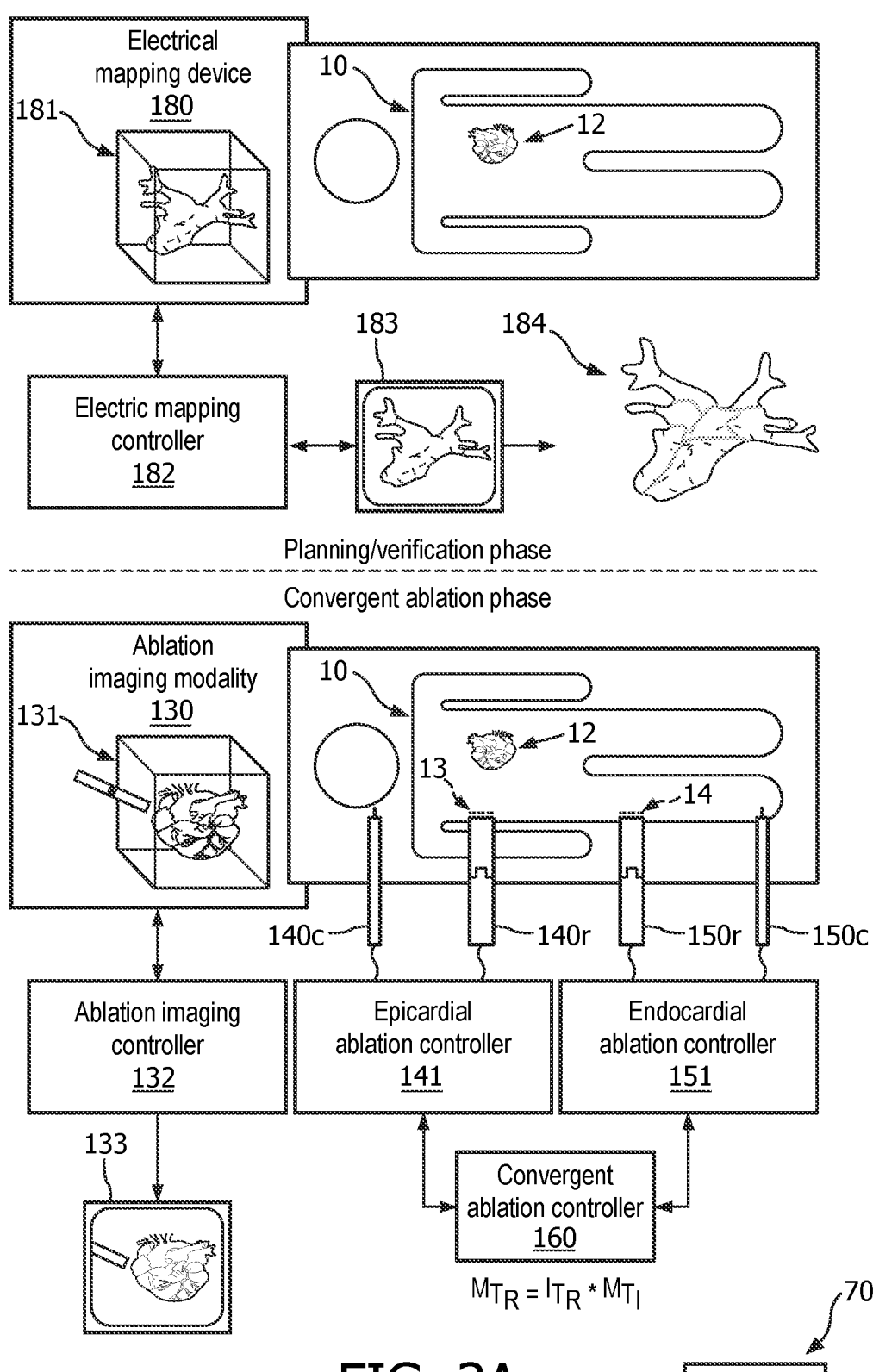
FIG. 3A illustrates an exemplary embodiment of convergent ablation system in accordance with the inventive principles of the present disclosure.

Referring to FIG. 3A, a planning/verification phase of the convergent ablation procedure incorporates an electric mapping system employing an electric mapping device 180, an electric mapping controller 182 and a monitor 183. Generally, electric mapping controller 182 controlling a generation by electric mapping device 180 of an electric map 181 of a heart 12 within a thoracic region of patient 10, and further controls a display as known in the art of electric map 181 of heart 12 on monitor 183 for planning and verification purposes as will be further explained herein, particularly a zoning electrical map 181 into an electrical isolation zone map 184.

Still referring to FIG. 3A, a convergent ablation phase of the convergent ablation procedure incorporates an ablation imaging system employing an ablation imaging modality 130 (e.g., a X-ray C-arm or a transesophageal echocardiography probe), an ablation imaging controller 132 and a monitor 133. The convergent ablation procedure further incorporates an epicardial ablation robot employing an ablation catheter 140c and an articulate robot 140r, an epicardial ablation controller 141, an endocardial ablation robot employing an ablation catheter 150c and an articulate robot 150r, an endocardial ablation controller 151 and a convergent ablation controller 160. The epicardial ablation robot and/or the endocardial ablation robot may further employ a catheter camera 70.

The convergent ablation procedure involves a single-port incision 13 into the thoracic region of patient 10 (e.g., between the ribs or subxypoid) whereby epicardial ablation controller 141 may autonomously control a navigation by articulated robot 140r of an ablation catheter 140c within the thoracic region of patient 10 in accordance with a epicardial ablation path generated by convergent ablation controller 160 as will be further described wherein. In practice, articulated robot 140c may support a navigation of camera catheter 70 alternatively or concurrently with ablation catheter 140r.

The convergent ablation procedure further involves a transfermoral incision 14 into a thigh of patient 10 whereby endocardial ablation controller 151 may autonomously control a navigation by articulated robot 150r of an ablation catheter 150c within the thoracic region of patient 10 in accordance with an endocardial ablation path generated by convergent ablation controller 160 as will be further described herein. In practice, similarly, articulated robot 150c may support a navigation of camera catheter 70 alternatively or concurrently with ablation catheter 150r.

To execute a convergent ablation of heart 12 as planned, the epicardial ablation robot and the endocardial ablation robot must be registered to electric map 181.

In one embodiment for the epicardial robot, articulated robot 140r supporting ablation catheter 140c (and optionally camera catheter 70) is manually or robotically inserted via a epicardial ablation controller 141 within the thoracic region of patient 10 adjacent heart 12 whereby ablation imaging controller 132 controls a generation by ablation imaging modality 131 of an ablation image 131 illustrative of articulated robot 140c relative to heart 12 within the thoracic region of patient 10. If camera catheter 70 is deployed via articulated robot 140c, then a camera catheter controller (not shown) controls a display an endoscopic video view of heart 12 via camera catheter 70 on monitor 133 or an additional monitor as known in the art for positioning purposes of articulated robot 140c relative to heart 12 of patient 10 and/or for registration purposes to electric map 181 and ablation image 131.

The registration of articulated robot 140c to electric map 181 is accomplished by convergent ablation controller 160 in accordance with the following equation [2a]:

$$^{M}T_{R} = {}^{I}T_{R} * {}^{M}T_{1} \qquad [2a]$$

where $^{I}T_{R}$ is the transformation of articulated robot 140r to ablation image 131, where $^{M}T_{I}$ is the transformation of anatomical image 121 to electric map 181, and where $^{M}T_{R}$ is the transformation of articulated robot 140r to electric map 181.

Still referring to FIG. 2A, upon the registration, epicardial ablation controller 141 is capable of autonomously controlling a navigation by articulated robot 140r of ablation catheter 140c within the thoracic region of patient 10 in accordance with the ablation path traversing an exterior of heart 12 as planned by convergent ablation catheter 160 as will be further explained herein. In practice, ablation catheter 140c may be a cyroablation catheter or a thermoablation catheter whereby an appropriate energy source (not shown) is controlled by epicardial ablation controller 141 to provide ablation catheter 140c with a specified degree of energy to perform the desired ablation of heart 12 as ablation catheter 140c is traversed across the exterior 11. During the ablation, ablation imaging controller 132 controls a display of the navigation of ablation catheter 140c within the thoracic region as known in the art for visual feedback purposes.

In one embodiment for the endocardial robot, articulated robot 150r supporting ablation catheter 150c (and optionally camera catheter 70) is manually or robotically inserted via a endocardial ablation controller 151 within the thoracic region of patient 10 adjacent heart 12 whereby ablation imaging controller 132 controls a generation by ablation imaging modality 130 of a ablation image 131 illustrative of articulated robot 150c relative to heart 12 within the thoracic region of patient 10. If camera catheter 70 is deployed via articulated robot 150c, then a camera catheter controller (not shown) controls a display an endoscopic video view of heart 12 via camera catheter 70 on monitor 133 or an additional monitor as known in the art for positioning purposes of articulated robot 150c relative to heart 12 of patient 10 and/or for registration purposes to electric map 181 and ablation image 131.

The registration of articulated robot 150c to electric map 181 is accomplished by convergent ablation controller 160 in accordance with the following equation [2b]:

$$^{M}T_{R} = {}^{I}T_{R} * {}^{M}T_{I} \quad [2b]$$

where $^{I}T_{R}$ is the transformation of articulated robot 150r to ablation image 131,
where $^{M}T_{I}$ is the transformation of anatomical image 121 to electric map 181, and
where $^{M}T_{R}$ is the transformation of articulated robot 150r to electric map 181.

Still referring to FIG. 2A, upon the registration, endocardial ablation controller 151 is capable of autonomously controlling a navigation by articulated robot 150r of ablation catheter 150c within the thoracic region of patient 10 in accordance with the ablation path traversing an interior of heart 12 as planned by convergent ablation catheter 160 as will be further explained herein. In practice, ablation catheter 150c may be a cyroablation catheter or a thermoablation catheter whereby an appropriate energy source (not shown) is controlled by endocardial ablation controller 151 to provide ablation catheter 150c with a specified degree of energy to perform the desired ablation of heart 12 as ablation catheter 150c is traversed across the interior 11. During the ablation, ablation imaging controller 132 controls a display of the navigation of ablation catheter 150c within the thoracic region as known in the art for visual feedback purposes.

Figures 3B, 4A:
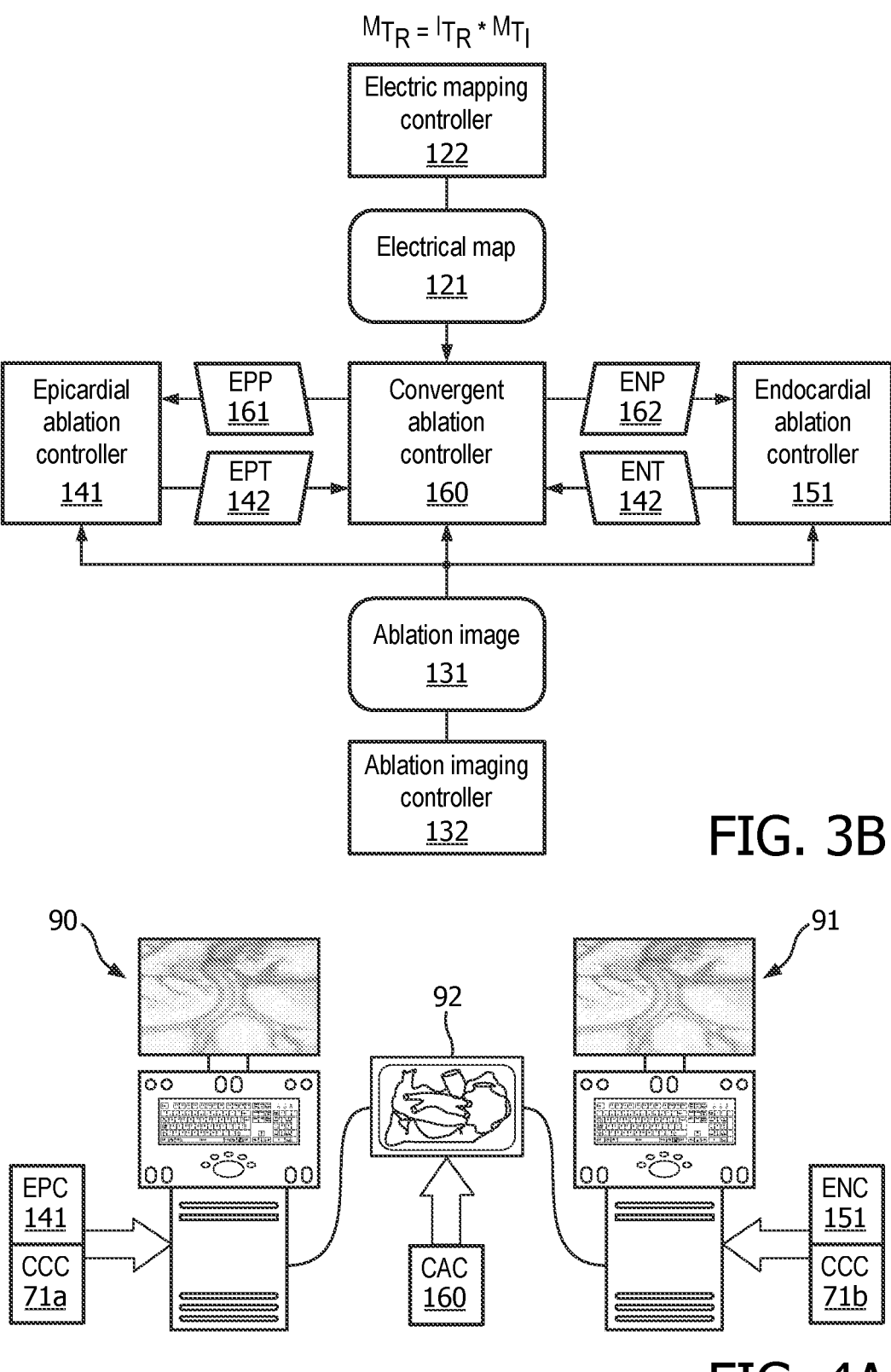
FIG. 3B illustrates an exemplary data/image flow between controllers of a convergent ablation system in accordance with the inventive principles of the present disclosure.
FIGS. 4A-4D illustrate four (4) exemplary embodiments of workstations in accordance with the inventive principles of the present disclosure.

With the registrations, the controllers implement a convergent ablation method as generally shown in FIG. 3B.

Referring to FIG. 3B, during the planning phase, convergent ablation controller 160 generates an epicardial ablation plan 161 and an endocardial ablation plan 162 by delineating two (2) or more electric isolation zones of electric map 181 of the heart generated by electric mapping controller 182.

Epicardial ablation plan 161 specifies an operation of epicardial ablation robot 140 to ablate an exterior of heart 12

(FIG. 3A) whereby epicardial ablation controller 141 controls a navigation of epicardial ablation robot 140 within the thoracic region relative to heart 12 as directed by epicardial ablation plan 161 under the image guidance of ablation image 131.

Similarly, endocardial ablation plan 162 specifies an operation of endocardial ablation robot 150 to ablate an interior of heart 12 whereby endocardial ablation controller 151 controls a navigation of endocardial ablation robot 150 within the thoracic region relative to heart 12 as directed by endocardial ablation plan 162 under the image guidance of ablation image 131.

During the ablation phase, convergent ablation controller 160 selectively initiates an epicardial ablation of heart 12 via a communication of epicardial ablation plan 161 to epicardial ablation controller 141 followed by an endocardial ablation of heart 12 via a communication of endocardial ablation plan 162 to endocardial ablation controller 151, or vice-versa. Furthermore, during the convergent ablation, convergent ablation controller 160 directs a single execution or multiple executions of epicardial ablation plan 161, and a single execution or multiple executions of endocardial ablation plan 162.

Convergent ablation controller 160 tracks the navigations of epicardial ablation robot 140 and endocardial ablation robot 150 within the thoracic region of heart 12 via ablation image 131 and/or an epicardial ablation report 142 and an endocardial ablation report 152, and revises plan epicardial ablation plan 161 and/or endocardial ablation plan 162 as needed to ensure a complete ablation of heart 12 as planned.

More particularly, if epicardial ablation robot 140 is incapable of being controlled by epicardial ablation controller 141 to completely execute epicardial ablation plan 161 for any reason as reported by epicardial ablation controller 141 and/or as illustrated within ablation image 131, then convergent ablation controller 160 will revise endocardial ablation plan 162 for endocardial ablation robot 150 as controlled by endocardial ablation controller 151 to perform a complementary ablation of any portion of epicardial ablation plan 161 not executed by epicardial ablation robot 140 as will be further described herein.

Conversely, if endocardial ablation robot 150 is incapable of being controlled by endocardial ablation controller 151 to completely execute endocardial ablation plan 162 for any reason as reported by endocardial ablation controller 151 and/or as illustrated within ablation image 131, then convergent ablation controller 160 will revise epicardial ablation plan 161 for epicardial ablation robot 140 as controlled by epicardial ablation controller 141 to perform a complementary ablation of any portion of endocardial ablation plan 162 not executed by endocardial ablation robot 150 as will be further described herein.

During a verification phase, convergent ablation controller 160 verifies a delineation of two (2) or more electric isolation zones of heart 12 as planned within a new electric map 181 of heart 12.

Upon completion, the execution of the convergent ablation procedure as shown in FIG. 3B results in a complete ablation of heart 12 as planned that impedes any future occurrences of an cardiac arrhythmia (e.g., atrial fibrillation) of heart 12.

In practice, the controllers of FIG. 3A may be installed within a single workstation or distributed across multiple workstations.

For example, FIG. 4A illustrates an epicardial ablation workstation 90 having epicardial ablation controller 141 installed therein, an endocardial ablation workstation 91 having endocardial ablation controller 151 installed therein, and a convergent ablation control pad 92 having convergent ablation controller 160 installed therein and linked to workstations 90 and 91 for control of controllers 141 and 151. If applicable, then a camera catheter controller 71 is installed on workstations 90 and/or 91.

Figure 4B:
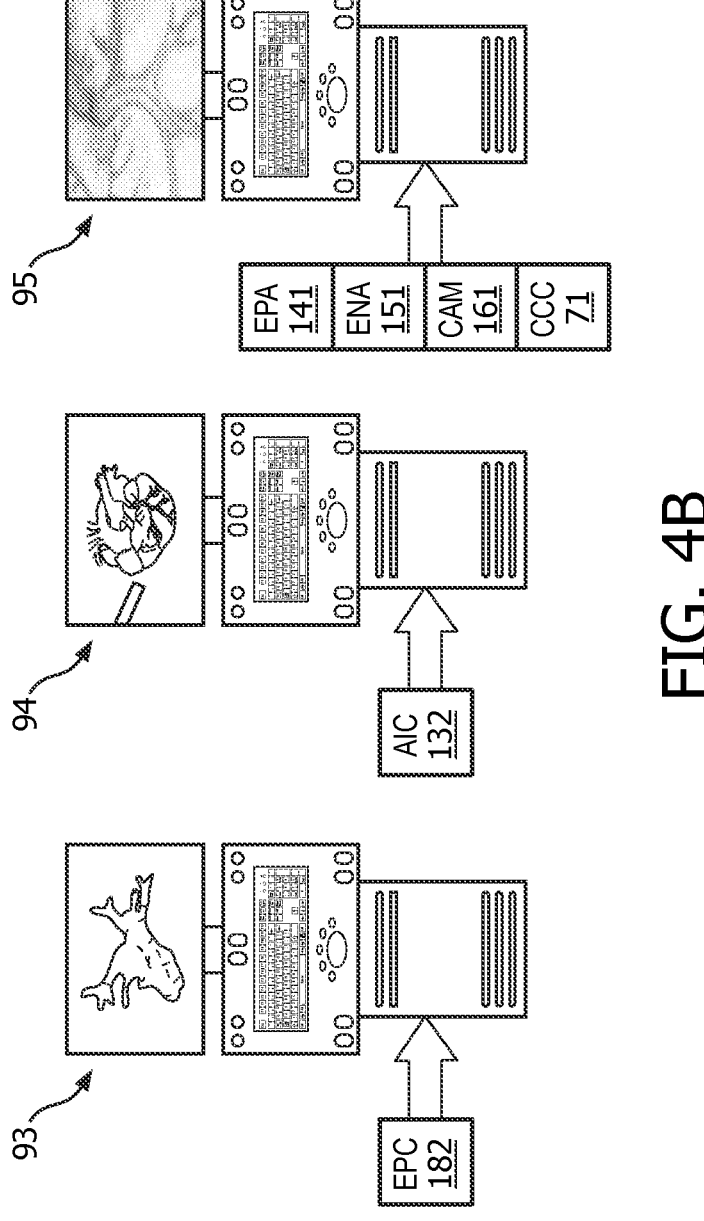

Also by example, FIG. 4B illustrates an electrical mapping workstation 93 having electric mapping controller 182 installed therein, and an ablation imaging workstation 94 having ablation imaging controller 132 installed therein. FIG. 4B further illustrates a convergent ablation workstation 95 having epicardial ablation controller 141, endocardial ablation controller 151, convergent ablation controller 160 and camera catheter controller 71 (if applicable) installed therein.

Figure 4C:
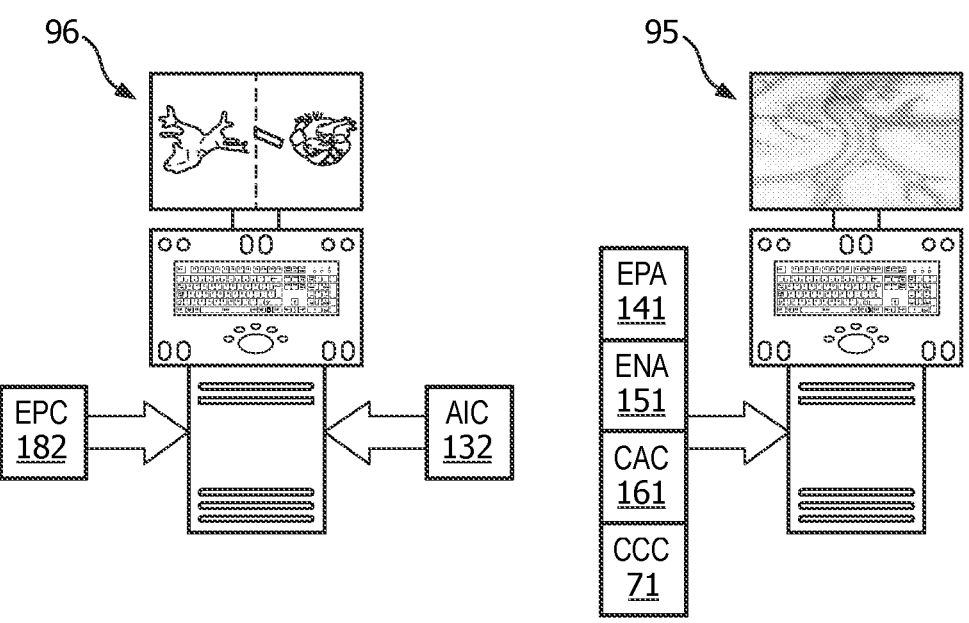

By further example, FIG. 4C illustrates a workstation 96 having both electric mapping controller 182 and ablation imaging controller 132 installed therein. FIG. 4C further illustrates ablation robot workstation 95.

Figure 4D:
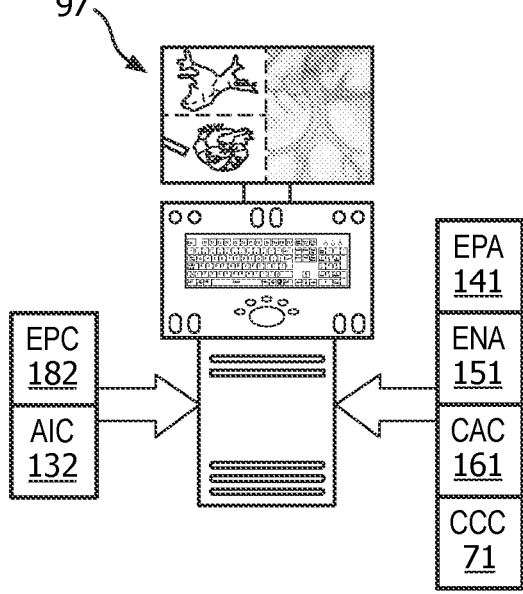

Even by further example, FIG. 4D illustrates a workstation 97 having all controllers of FIG. 3A installed therein.

Figure 5:
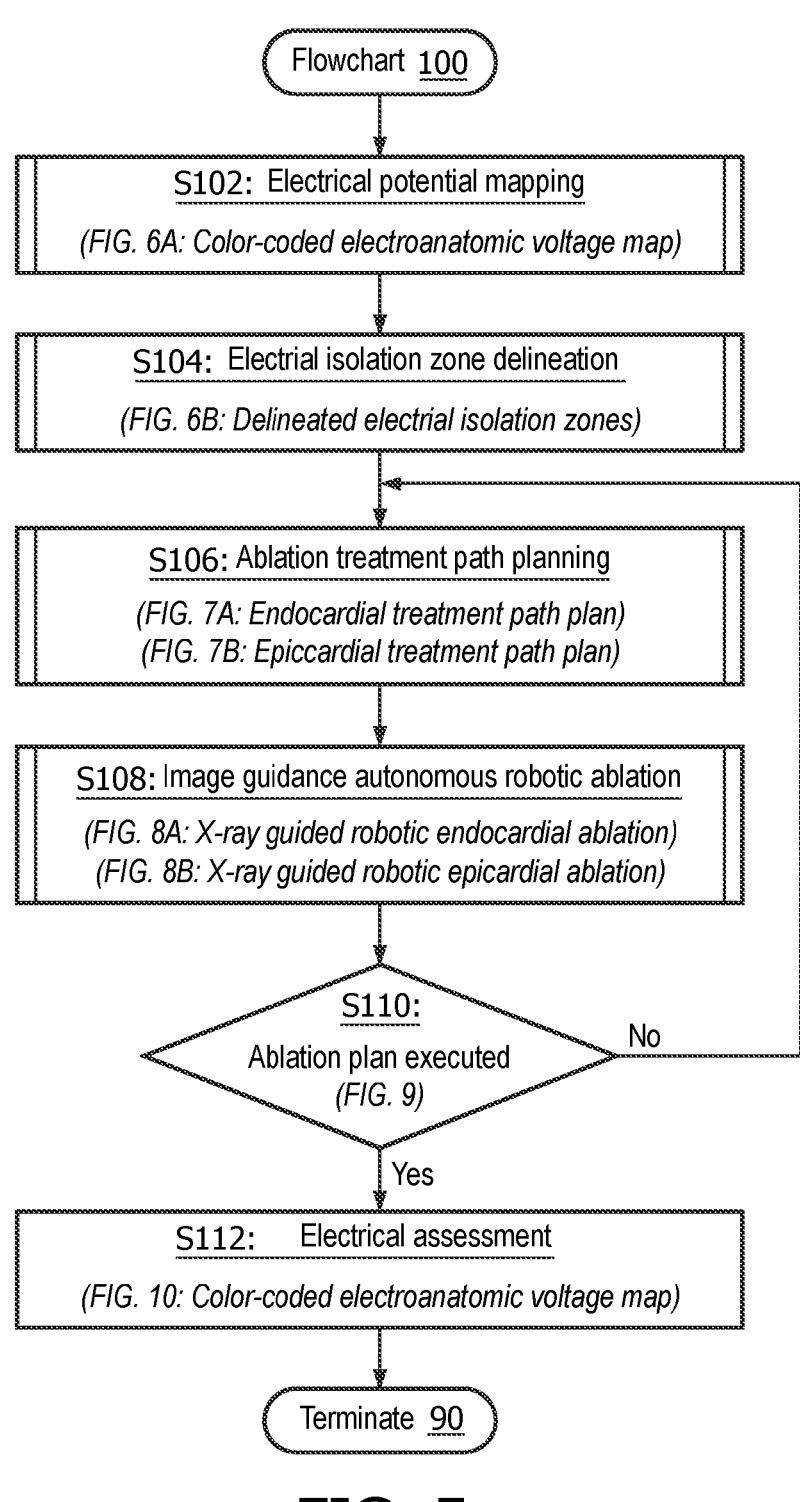
FIG. 5 illustrates a flowchart representative of an exemplary embodiment of a convergent ablation method in accordance with the inventive principles of the present disclosure.

To facilitate a further understanding of the present disclosure, the following description of FIG. 5 teaches basic inventive principles of a convergent ablation method of the present disclosure as represented by a flowchart 100. From this description, those having ordinary skill in the art will appreciate how to apply the inventive principles of the present disclosure to for any type of hybrid procedure.

Referring to FIG. 5, a stage S102 of flowchart 100 encompasses a mapping of an electrical potential of heart 12 (FIG. 3A) as controlled by electric mapping controller 182 (FIG. 3A).

Figure 6A:
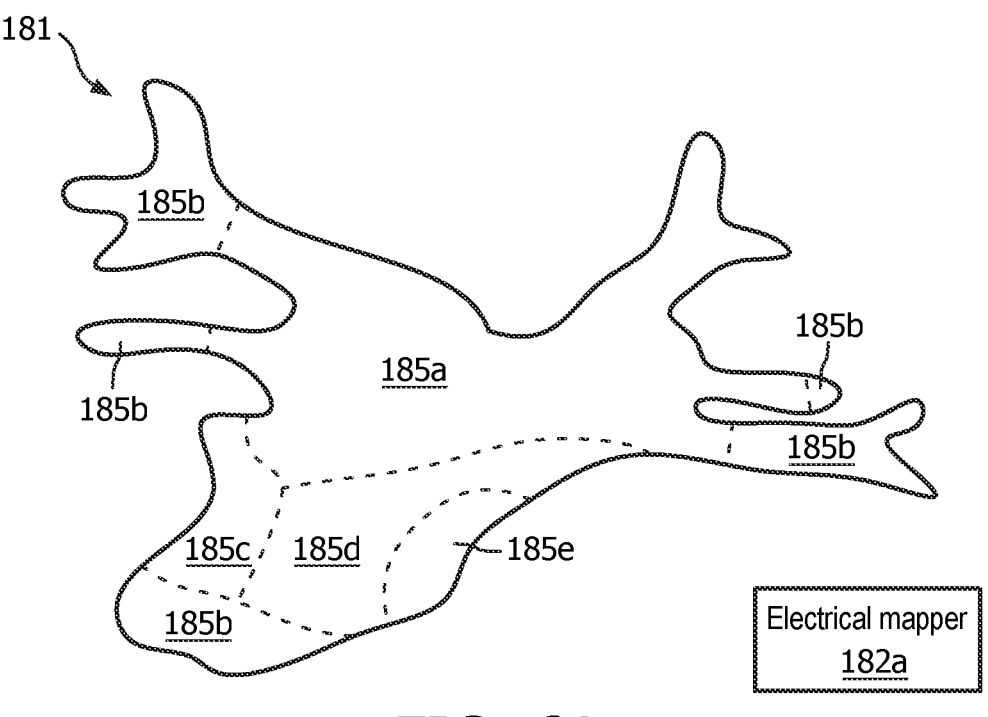
FIG. 6A illustrates an exemplary electrical potential mapping in accordance with the inventive principles of the present disclosure.

In one embodiment, electric mapping controller 182 generates a color-coded electroanatomic voltage map of heart 12 using an electrophysiology technique known in the art. For example, FIG. 6A illustrates a generation by an electrical mapper module 182a of electric mapping controller 182 of a color-coded electroanatomic voltage map 181 having different voltage potentials 185a-185e.

Figure 6B:
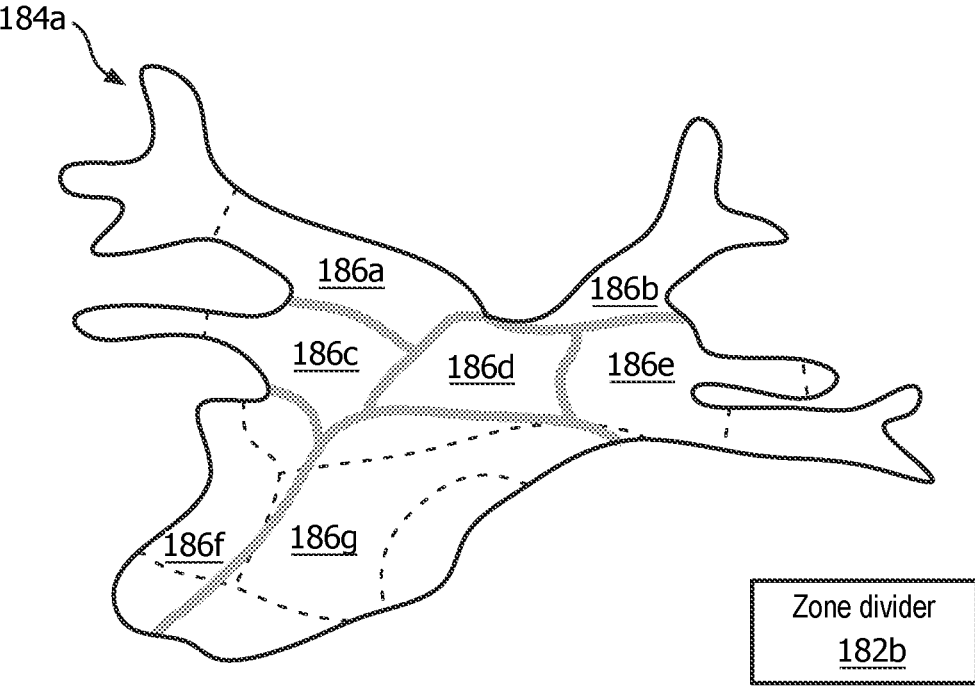
FIG. 6B illustrates an exemplary electrical isolation zone delineation in accordance with the inventive principles of the present disclosure.

Referring back to FIG. 5, a stage S104 of flowchart 100 encompasses an operator delineation of electrical isolation zones within electric map 181 of heart 12 via an interface provided by electric mapping controller 182 or alternatively convergent ablation controller 160. For example, as shown FIG. 6B, a zone divider module 182b of electric mapping controller 182 provided an interface whereby an operator by delineates electrical isolation zones 186a-186g within electric map 181 to render an electric isolation zone map 184a.

Referring back to FIG. 5, a stage S106 of flowchart 100 encompasses path planning of an ablation treatment of heart 12 involving an epicardial ablation and an endocardial ablation.

In practice, convergent ablation controller 160 identifies trajectories for the respective robots to meet the isolation zones. The path planning of stage S106 takes into account the relative 'strengths and weaknesses' of the different ablation approaches and robot architectures, and may further take into account the optimum access points for both robots.

Figure 7A:
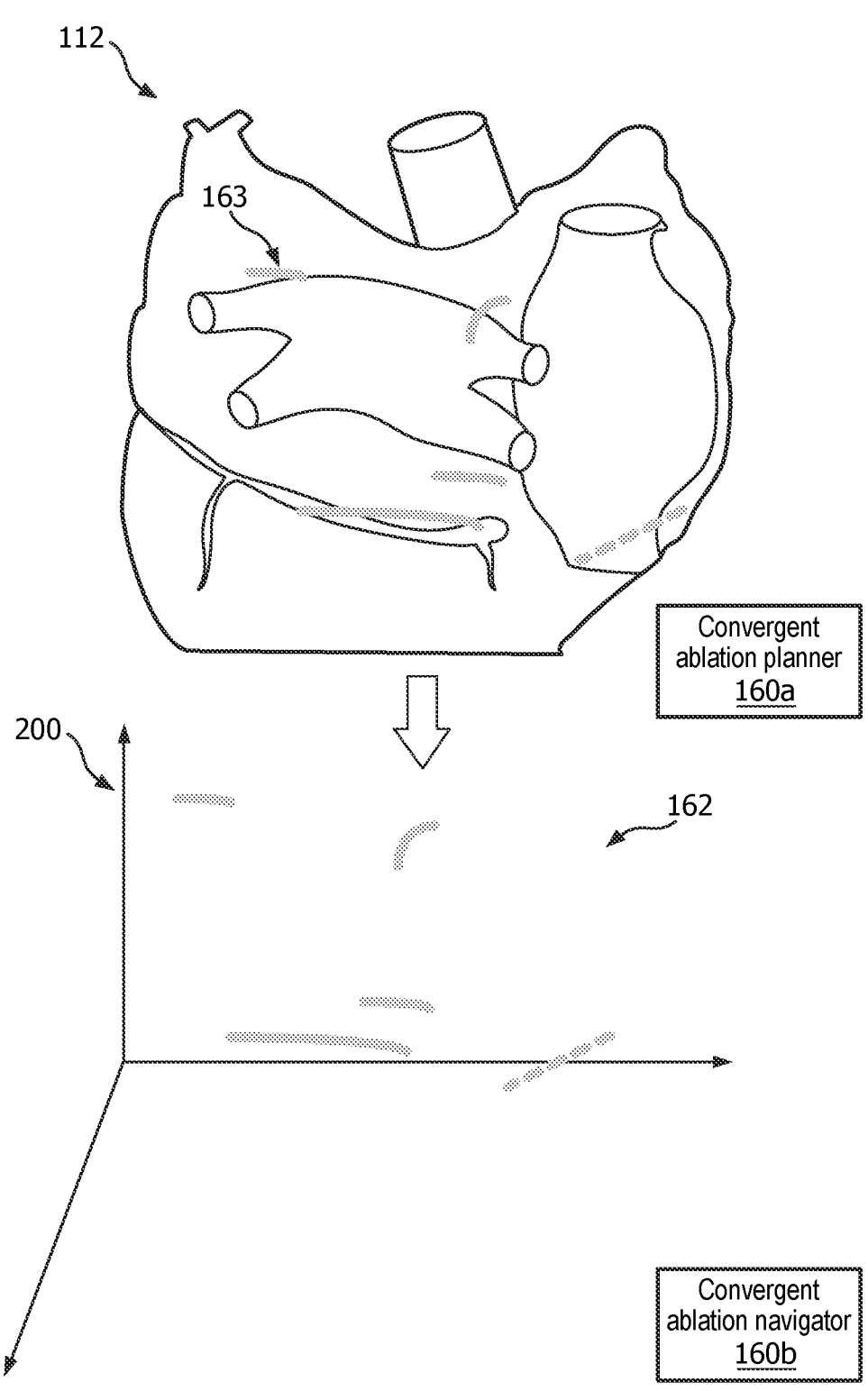
FIG. 7A illustrates an exemplary an endocardial ablation planning in accordance with the inventive principles of the present disclosure.

For the endocardial ablation, as shown in FIG. 7A, a convergent ablation planner module 160a of convergent ablation controller 160 identifies trajectories 163 relative to a planned model 112 of heart 12, and a convergent ablation navigator 160b transforms trajectories 163 into endocardial plan 162 for navigating the endocardial robot within a coordinate system 200 representative of the image/robot registrations.

Figure 7B:
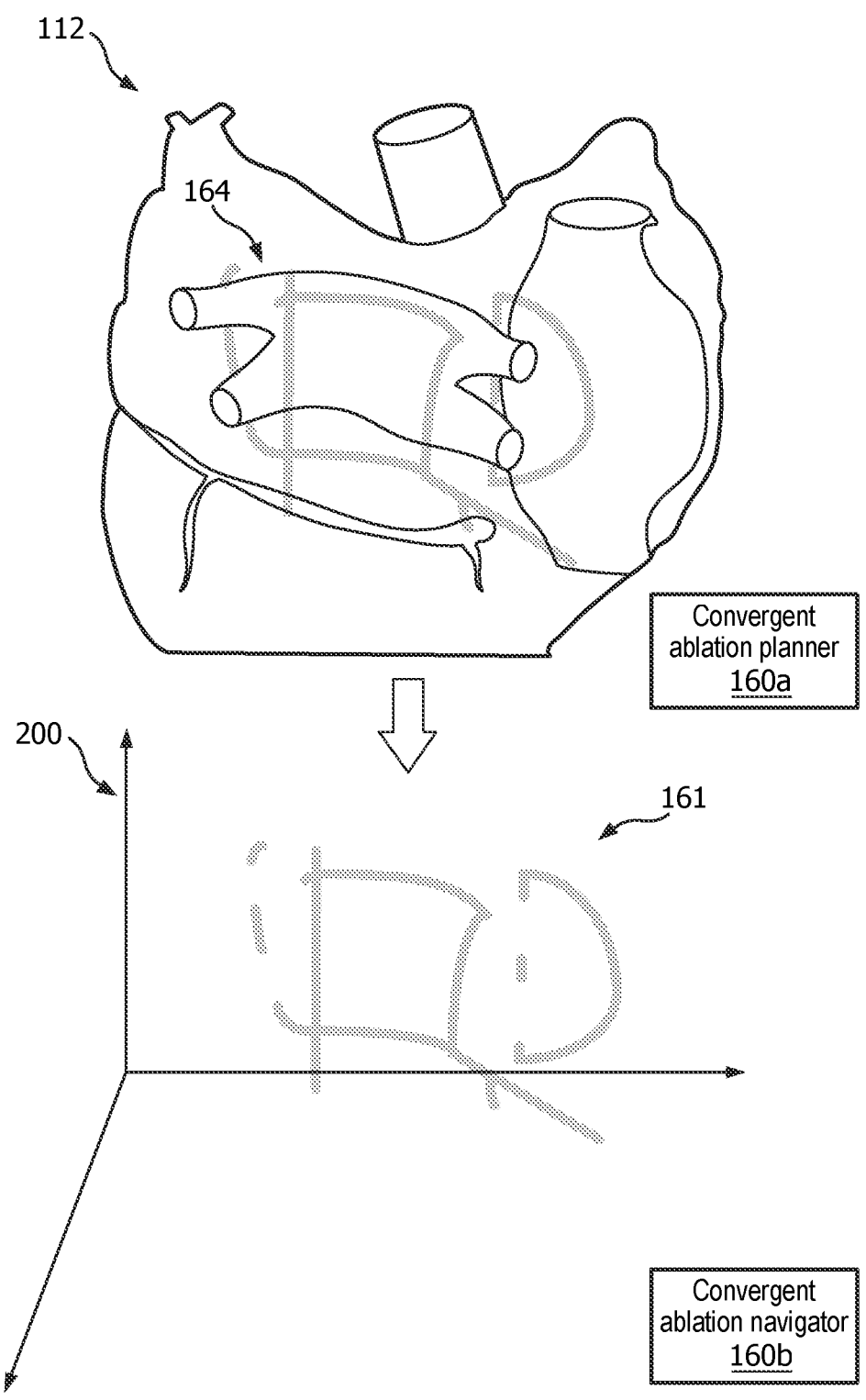
FIG. 7B illustrates an exemplary an epicardial ablation planning in accordance with the inventive principles of the present disclosure.

For the epicardial ablation, as shown in FIG. 7B, convergent ablation planner module 160a of convergent ablation controller 160 identifies trajectories 164 relative to planned model 112 of heart 12, and convergent ablation navigator 160b transforms trajectories 164 into endocardial plan 161 for navigating the epicardial robot within coordinate system 200 representative of the image/robot registrations.

Referring back to FIG. 5, a stage S108 of flowchart 100 encompasses an endocardial ablation under live image guidance followed by an epicardial ablation under live image guidance, or vice-versa.

Figure 8:
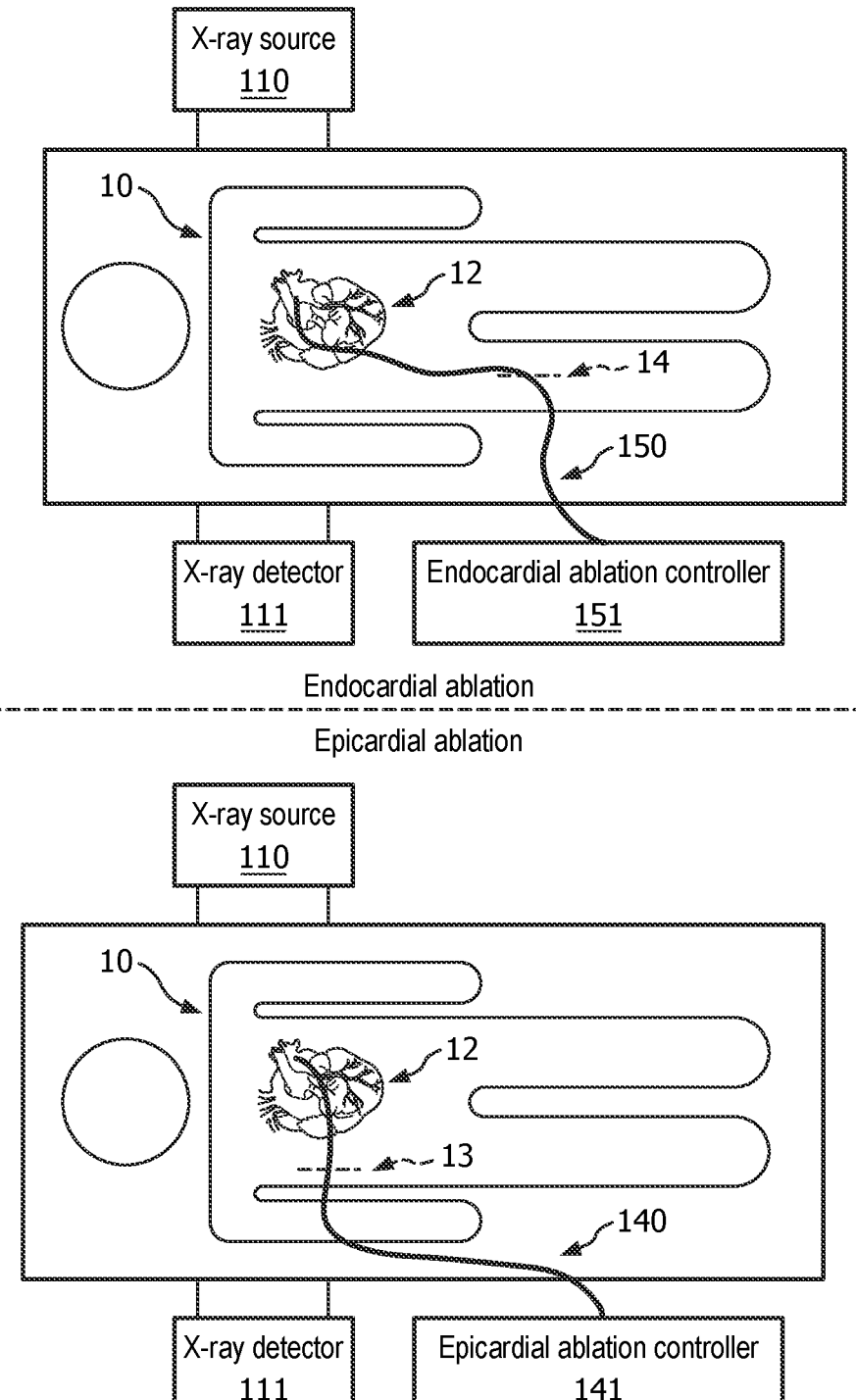
FIG. 8 illustrates an exemplary an convergent surgery in accordance with the inventive principles of the present disclosure.

For example, as shown in FIG. 8, an X-ray source 110 and an X-ray detector 111 of a C-arm provide live image guidance for the endocardial ablation and the epicardial ablation.

Figures 9, 10:
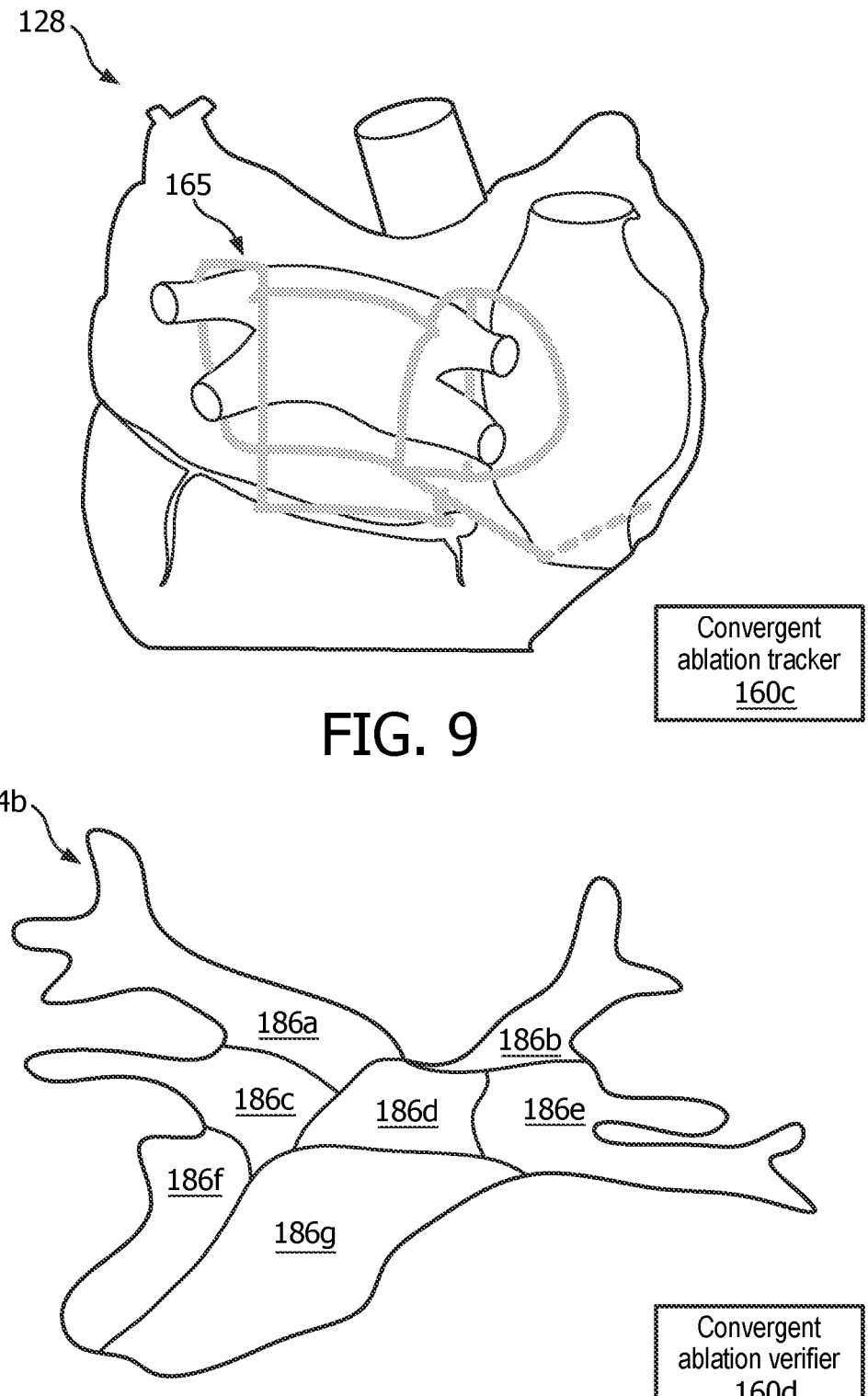
FIG. 9 illustrates an exemplary a convergent ablation in accordance with the inventive principles of the present disclosure.
FIG. 10 illustrates an exemplary electrical isolation zone verification in accordance with the inventive principles of the present disclosure.

Referring back to FIG. 5, a stage S110 of flowchart 100 encompasses a determination by convergent ablation controller 160 whether epicardial ablation plan 161 and endocardial ablation plan 162 were fully executed. To this end, as shown in FIG. 9, a convergent ablation tracker 160c of convergent ablation controller 160 ascertains whether epicardial ablation plan 161 and endocardial ablation plan 162 were fully executed via images of the ablations and/or reporting of the ablations as previously described herein.

More particularly, if epicardial ablation robot 140 is incapable of being controlled by epicardial ablation controller 141 to completely execute epicardial ablation plan 161 for any reason as reported by epicardial ablation controller 141 and/or as illustrated within ablation image 131, then convergent ablation controller 160 returns to stage S106 to revise endocardial ablation plan 162 for endocardial ablation robot 150 as controlled by endocardial ablation controller 151 to perform a complementary interior ablation of heart 12 for any portion of epicardial ablation plan 161 not executed by epicardial ablation robot 140.

Conversely, if endocardial ablation robot 150 is incapable of being controlled by endocardial ablation controller 151 to completely execute endocardial ablation plan 162 for any reason as reported by endocardial ablation controller 151 and/or as illustrated within ablation image 131, then convergent ablation controller 160 returns to stage S106 to revise epicardial ablation plan 161 for epicardial ablation robot 140 as controlled by epicardial ablation controller 141 to perform a complementary exterior ablation of heart 12 of any portion of endocardial ablation plan 162 not executed by endocardial ablation robot 150.

Convergent ablation controller 160 loops through stages S106-S110 until the full ablation is completed as planned.

Upon full ablation as planned, a stage S112 of flowchart 100 encompasses an assessment of ablation by generation of a new electric mapping of heart 12. As shown in FIG. 10, a convergent ablation verifier module 160d, reviews the new electric map 184b to ensure electrical isolation zones 186a-186g were delineated with heart 12 via ablation as planned.

Referring back to FIG. 5, flowchart 100 is terminated upon a satisfactory assessment or may be repeated to any degree as necessary.

Referring to FIGS. 1-10, those having ordinary skill in the art will appreciate numerous benefits of the present disclosure including, but are not limited to, the novel and unique robotic control for any type of hybrid procedure incorporating image guidance based autonomous robotic control of two (2) or more complementary surgical procedures. on any anatomical structure (e.g., a heart, a liver, a kidney and a bone structure).

Furthermore, as one having ordinary skill in the art will appreciate in view of the teachings provided herein, features, elements, components, etc. described in the present disclosure/specification and/or depicted in the FIGS. 1-10 may be implemented in various combinations of electronic components/circuitry, hardware, executable software and executable firmware and provide functions which may be combined in a single element or multiple elements. For example, the functions of the various features, elements, components, etc. shown/illustrated/depicted in the FIGS. 1-10 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive robotic control of a surgical procedure (which embodiments are intended to be illustrative and not limiting), it is noted that modifications and variations can be made by persons having ordinary skill in the art in light of the teachings provided herein, including the FIGS. 1-10. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A robotic system for executing a surgical procedure on an anatomical structure within an anatomical region, the robotic system comprising:

a plurality of surgical robots including a first surgical robot and a second surgical robot;

a surgical procedure controller configured to autonomously control a navigation of the first surgical robot within the anatomical region relative to the anatomical structure and the second surgical robot within the anatomical region relative to the anatomical structure, the surgical procedure controller configured to:

generate a first surgical plan for executing a first portion of the surgical procedure by the first surgical robot and a second surgical plan, that is different from the first surgical plan, for executing a second portion of the surgical procedure by the second surgical robot;

autonomously direct the navigation of the first surgical robot within the anatomical region relative to the anatomical structure based on the first surgical plan and the navigation of the second surgical robot within the anatomical region relative to the anatomical structure based on the second surgical plan, autonomously ascertain whether the first surgical plan has been fully executed by the first surgical robot during the first portion of the surgical procedure, and responsive to the first surgical plan having not been fully executed by the first surgical robot of the plurality of surgical robots, revise the second surgical plan during the surgical procedure to navigate the second surgical robot to autonomously perform a complementary execution of a portion of the first surgical plan unexecuted by the first surgical robot; and an imaging controller configured to control a generation of a first image illustrative of the navigation of the first surgical robot within the anatomical region relative to the anatomical structure, wherein the surgical procedure controller ascertains whether the first surgical plan has been fully executed by the first surgical robot as illustrated within the first image.

2. The robotic system of claim 1,
wherein at least one of:
the first surgical robot comprises an epi-surgical robot,
the first surgical plan comprises an epi-surgical plan,
the second surgical robot comprises an endo-surgical
robot, and the second surgical plan comprises an
endo-surgical plan; or
the first surgical robot comprises the endo-surgical
robot, the first surgical plan comprises the endo-
surgical plan, the second surgical robot comprises
the epi-surgical robot, and the second surgical plan
comprises the epi-surgical plan; and
wherein the surgical procedure controller is a hybrid
procedure controller.
3. The robotic system of claim 2, further comprising:
an anatomical mapping controller configured to:
control a generation of an anatomical map of the
anatomical structure, and
derive the epi-surgical plan and the endo-surgical plan
from a planned delineation of the anatomical map of
the anatomical structure into at least two zones.
4. The robotic system of claim 2, wherein the imaging
controller comprises an anatomical imaging controller con-
figured to at least one of:
control a generation of an epi-surgical anatomical image
illustrative of a navigation of the epi-surgical robot
within the anatomical region relative to the anatomical
structure, and
control a generation of an endo-surgical anatomical image
illustrative of a navigation of the endo-surgical robot
within the anatomical region relative to the anatomical
structure; and
wherein at least one of the hybrid procedure controller
and the anatomical imaging controller is further con-
figured to:
as illustrated within the epi-surgical anatomical image,
ascertain whether the epi-surgical plan has been fully
executed by the epi-surgical robot to be navigated
within the anatomical region relative to the anatomical
structure, and
as illustrated within the endo-surgical anatomical image,
ascertain whether the endo-surgical plan has been fully
executed by the endo-surgical robot to be navigated
within the anatomical region relative to the anatomical
structure based on the endo-surgical plan.
5. The robotic system of claim 2, further comprising:
at least one of an epi-surgical controller and an endo-
surgical controller, wherein the epi-surgical controller
is configured to:
control the navigation of the epi-surgical robot within
the anatomical region relative to the anatomical
structure as directed by the hybrid procedure con-
troller, and
communicate an epi-surgical report to the hybrid pro-
cedure controller, the epi-surgical report being informative of the epi-surgical plan not having been fully
executed by the epi-surgical robot to be navigated by
the epi-surgical controller within the anatomical
region relative to the anatomical structure based on
the epi-surgical plan, and
wherein the endo-surgical controller is configured to:
control the navigation of the endo-surgical robot
within the anatomical region relative to the ana-
tomical structure as directed by the hybrid proce-
dure controller, and
communicate an endo-surgical report to the hybrid
procedure controller, the endo-surgical report being informative of the endo-surgical plan not
having been fully executed by the endo-surgical
robot to be navigated by the endo-surgical con-
troller within the anatomical region relative to the
anatomical structure based on the endo-surgical
plan.
6. The robotic system of claim 2,
wherein the epi-surgical robot is an epicardial ablation
robot;
wherein the epi-surgical plan is an epicardial ablation plan
for operating the epicardial ablation robot to ablate an
exterior of a heart;
wherein the endo-surgical robot is an endocardial ablation
robot;
wherein the endo-surgical plan is an endocardial ablation
plan for operating the endocardial ablation robot to
ablate an interior of the heart; and
wherein the anatomical region relative to the anatomical
structure is a thoracic region relative to a heart.
7. The robotic system of claim 6, further comprising:
an electrical mapping controller configured to:
control a generation of an electrical map of the heart,
and
at least one of:
derive the epicardial ablation plan and the endocar-
dial ablation plan from a planned delineation of
the electrical map of the heart into at least two
electrical isolation zones, and
assess, within the electric map of the heart, at least
one ablated delineation of the heart into at least
two electrical isolation zones by at least one of an
operation of the epicardial ablation robot based on
the epicardial ablation plan and an operation of the
endocardial ablation robot based on the endocar-
dial ablation plan.
8. The robotic system of claim 6, wherein the imaging
controller comprises an ablation imaging controller config-
ured to at least one of:
control a generation of an epicardial ablation image
illustrative of a navigation of the epicardial ablation
robot within the thoracic region relative to the heart, or
control a generation of an endocardial ablation image
illustrative of a navigation of the endocardial ablation
robot within the thoracic region relative to the heart;
and
wherein at least one of a convergent ablation controller
and the ablation imaging controller is further config-
ured to:
as illustrated within the epicardial ablation image,
ascertain whether the epicardial ablation plan has
been fully executed by the epicardial ablation robot
to be navigated within the thoracic region relative to
the heart; and
as illustrated within the endocardial ablation image,
ascertain whether the endocardial ablation plan has
been fully executed by the endocardial ablation robot
to be navigated within the thoracic region relative to
the heart.
9. The robotic system of claim 6, further comprising:
at least one of an epicardial ablation controller and an
endocardial ablation controller, wherein the epicardial
ablation controller is configured to:
control the navigation of the epicardial ablation robot
within the thoracic region relative to the heart as
directed by a convergent ablation controller, and
communicate an epicardial ablation report to the con-
vergent ablation controller, the epicardial ablation report being informative of the epicardial ablation plan not having been fully executed by the epicardial ablation robot to be navigated by the epicardial ablation controller within the thoracic region relative to the heart based on the epicardial ablation plan; and wherein the endocardial ablation controller is configured to:

control the navigation of the endocardial ablation robot within the thoracic region relative to the heart as directed by the convergent ablation controller, and communicate an endocardial ablation report to the hybrid procedure controller, the endocardial ablation report being informative of the endocardial ablation plan not having been fully executed by the endocardial ablation robot to be navigated by the endocardial ablation controller within the thoracic region relative to the heart based on the endocardial ablation plan.

10. A surgical procedure controller for autonomously controlling a navigation of a plurality of surgical robots within an anatomical region relative to an anatomical structure, the surgical procedure controller comprising:

at least one processor configured to:

generate a first surgical plan for executing a first portion of a surgical procedure on the anatomical structure by a first surgical robot and a second surgical plan, that is different than the first surgical plan for executing a second portion of the surgical procedure on the anatomical structure by a second surgical robot;

autonomously direct a navigation of the first surgical robot within the anatomical region relative to the anatomical structure based on the first surgical plan and a navigation of the second surgical robot within the anatomical region relative to the anatomical structure based on the second surgical plan;

autonomously ascertain whether the first surgical plan has been fully executed by the first surgical robot during the first portion of the surgical procedure as illustrated within a first image illustrative of the navigation of the first surgical robot within the anatomical region relative to the anatomical structure; and responsive to the first surgical plan having not been fully executed by the first surgical robot, revise the second surgical plan during the surgical procedure to autonomously navigate the second surgical robot of to perform a complementary execution of a portion of the first surgical plan unexecuted by the first surgical robot.

11. The surgical procedure controller of claim 10, wherein at least one of:

the first surgical robot comprises an epi-surgical robot and the first surgical plan comprises an epi-surgical plan, the second surgical robot comprises an endo-surgical robot, and the second surgical plan comprises an endo-surgical plan; or first surgical robot comprises an endo-surgical robot, the first surgical plan comprises an endo-surgical plan, the second surgical robot comprises an epi-surgical robot, and the second surgical plan comprises an epi-surgical plan.

12. The surgical procedure controller of claim 11, wherein the at least one processor is further configured to derive the epi-surgical plan and the endo-surgical plan from a delineation of a map of the anatomical structure into at least two isolation zones.

13. The surgical procedure controller of claim 11, wherein the at least one processor is further configured to at least one of:

ascertain whether the epi-surgical plan has been fully executed by the epi-surgical robot to be navigated within the anatomical region relative to the anatomical structure as illustrated within an epi-surgical image of the navigation of the epi-surgical robot within the anatomical region relative to the anatomical structure; or ascertain whether the endo-surgical plan has been fully executed by the endo-surgical robot to be navigated within the anatomical region relative to the anatomical structure as illustrated within an endo-surgical image of the navigation of the endo-surgical robot within the anatomical region relative to the anatomical structure.

14. The surgical procedure controller of claim 11, wherein the at least one processor is further configured to at least one of:

ascertain whether the epi-surgical plan has been fully executed by the epi-surgical robot to be navigated within the anatomical region relative to the anatomical structure responsive to an epi-surgical report; or ascertain whether the endo-surgical plan has been fully executed by the endo-surgical robot to be navigated within the anatomical region relative to the anatomical structure responsive to an endo-surgical report.

15. The surgical procedure controller of claim 11, wherein the epi-surgical robot is an epicardial ablation robot;

wherein the epi-surgical plan is an epicardial ablation plan for operating the epicardial ablation robot to ablate an exterior of a heart;

wherein the endo-surgical robot is an endocardial ablation robot;

wherein the endo-surgical plan is an endocardial ablation plan for operating the endocardial ablation robot to ablate an interior of the heart; and wherein the anatomical region relative to the anatomical structure is a thoracic region relative to a heart.

16. A method for autonomously controlling a navigation of a plurality of surgical robots within an anatomical region relative to an anatomical structure, the method comprising:

generating a first surgical plan for executing a first portion of a surgical procedure by a first surgical robot and a second surgical plan, that is different than the first surgical plan, for executing a second portion of the surgical procedure by a second surgical robot;

autonomously directing a navigation of the first surgical robot within the anatomical region relative to the anatomical structure based on the first surgical plan and a navigation of the second surgical robot within the anatomical region relative to the anatomical structure based on the second surgical plan, controlling a generation of a first image illustrative of the navigation of the first surgical robot within the anatomical region relative to the anatomical structure;

as illustrated within the first image, autonomously ascertaining whether the first surgical plan has been fully executed by the first surgical robot to be navigated within the anatomical region relative to the anatomical structure during the first portion of the first surgical plan; and responsive to the first surgical plan having not been fully executed by the first surgical robot, revising the second surgical plan during the surgical procedure to autonomously navigate the second surgical robot to perform a complementary execution a portion of the first surgical plan unexecuted by the first surgical robot.

17. The method of claim 16, further comprising:

generating the first surgical plan and the second surgical plan from a delineation of the anatomical structure into at least two isolation zones.

18. The method of claim 16, further comprising:

ascertaining whether the first surgical plan has been fully executed by the first surgical robot to be navigated within the anatomical region relative to the anatomical structure from a report informative of the navigation of the first surgical robot within the anatomical region relative to the anatomical structure.

19. The method of claim 16, wherein at least one of:

the first surgical robot comprises an epi-surgical robot and the first surgical plan comprises an epi-surgical plan, the second surgical robot comprises an endo-surgical robot, and the second surgical plan comprises an endo-surgical plan; or the first surgical robot comprises an endo-surgical robot, the first surgical plan comprises an endo-surgical plan, the second surgical robot comprises an epi-surgical robot, and the second surgical plan comprises an epi-surgical plan.

20. The method of claim 16, wherein at least one of:

the first surgical robot comprises an epicardial ablation robot, the first surgical plan comprises an epicardial ablation plan for ablating an exterior of a heart, the second surgical robot comprises an endocardial ablation robot, and the second surgical plan comprises an endocardial ablation plan for ablating in interior of the heart; or the first surgical robot comprises an endocardial ablation robot, the first surgical plan comprises endocardial ablation plan for ablating in interior of the heart, the second surgical robot comprises an epicardial ablation robot, and the second surgical plan comprises an epicardial ablation plan for ablating an exterior of the heart, wherein the anatomical region relative to the anatomical structure is a thoracic region relative to a heart.

* * * * *